US006299582B1

(12) United States Patent
Brockway et al.

(10) Patent No.: US 6,299,582 B1
(45) Date of Patent: *Oct. 9, 2001

(54) RESPIRATION MONITORING SYSTEM BASED ON SENSED BLOOD PRESSURE VARIATIONS

(75) Inventors: Brian P. Brockway, Arden Hills; Robert V. Brockway, Maple Grove; Richard A. Fundakowski, St. Paul, all of MN (US)

(73) Assignee: Data Sciences International, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 08/819,888

(22) Filed: Mar. 18, 1997

Related U.S. Application Data

(63) Continuation of application No. 08/535,656, filed on Sep. 28, 1995, now abandoned.

(51) Int. Cl.[7] .................................................. A61B 5/00

(52) U.S. Cl. .......................... 600/484; 600/485; 600/500; 600/529

(58) Field of Search .................................. 600/483–486, 600/490, 493, 500–502, 529, 538, 543, 561, 481

(56) References Cited

U.S. PATENT DOCUMENTS

| | | |
|---|---|---|
| 4,031,884 | 6/1977 | Henzel . |
| 4,667,680 | 5/1987 | Ellis . |
| 4,677,984 | * 7/1987 | Sramek ............................... 128/681 |
| 4,686,987 | 8/1987 | Salo et al. . |

(List continued on next page.)

FOREIGN PATENT DOCUMENTS

| | | |
|---|---|---|
| 0 503 839 B1 | 8/1998 | (EP) . |
| 96/14968 | 5/1996 | (WO) . |

OTHER PUBLICATIONS

Rubini et al., "Power Spectrum Analysis of Cardiovascular Variability Monitored by Telemetry in Conscious Unrestrained Rats," Journal of Autonomic Nervous System, 45, 1993, pp. 181–190.*

Bartholmes, et al., "A Device with Digital Display for the Determination of Respiratory Frequency from the Respiratory Fluctuations of Blood Pressure," *Biomedizinische Technik* vol. 18, 4 (Aug. 1973) 5 pp. plus 5 page translation.

Laude, et al., "Effect of Breathing Pattern on Blood Pressure and Heart Rate Oscillations in Humans," *Laboratoire de Pharmacologie*, CNRS URA, (1993) 619–626.

Öri, et al., "Heart Rate Variability–Frequency Domain Analysis" *Anuulatory Electrocardiography* vol. 10 No. 3 (Aug. 1992) 499–597.

(List continued on next page.)

*Primary Examiner*—Robert L. Nasser
(74) *Attorney, Agent, or Firm*—Schwegman, Lundberg, Woessner & Kluth, P.A.

(57) ABSTRACT

A system and method obtains physiologic parameter information of an animal or human, such as respiratory rate, from a blood pressure signal from an implanted blood pressure sensor in the animal or human. Specifically, the blood pressure signal is externally signal processed to develop an amplitude versus time waveform. A sequence of selected blood pressure features derived from individual cardiac cycles of the amplitude versus time waveform over a selected time interval are extracted from the developed amplitude versus time waveform. A mathematical model is fitted to the extracted sequence of selected blood pressure features to yield a fitted mathematical model. The physiologic parameter information is computed from the fitted mathematical model.

23 Claims, 3 Drawing Sheets

U.S. PATENT DOCUMENTS

| | | | | |
|---|---|---|---|---|
| 4,799,491 | * | 1/1989 | Eckerle | 128/672 |
| 4,805,629 | | 2/1989 | Farges | 600/484 |
| 4,846,191 | * | 7/1989 | Brockway et al. | 600/486 |
| 4,860,759 | | 8/1989 | Kahn et al. | 128/668 |
| 4,901,725 | | 2/1990 | Nappholz et al. | 128/419 |
| 5,265,615 | * | 11/1993 | Frank et al. | 128/672 |
| 5,391,190 | | 2/1995 | Pederson et al. | 607/23 |
| 5,682,898 | | 11/1997 | Aung et al. | |
| 5,769,082 | | 6/1998 | Perel | 600/484 |
| 5,980,463 | * | 11/1999 | Brockway et al. | 600/484 |

OTHER PUBLICATIONS

Novak, et al., "Influence of reapiration on heart rate and blood pressure fluctations," *American Physiological Society* (1993) 617–625.

Rubini, et al., "Power spectrum analysis of cardiovascular variablility monitored by telemetry in conscious unrestrained rats," *Journal of Automatic Nervous System* 45 (1993) 181–190.

Womack, Baxter F., "The Analysis of Respiratory Sinus Arrhythmia Using Spectral Analysis and Digital Filtering," *IEEE Transactions on Bio–Medical Engineering*, vol. BME–18, No. 6 (Nov. 1971), pp. 399–409.

"Circulatory Effects of Respiration", *Medical Physiology, vol. I*, Vernon B. Mountcastle, M.D., Twelfth edition, pp. 217–220, (1968).

* cited by examiner

RESPIRATION MONITORING SYSTEM BASED ON SENSED BLOOD PRESSURE VARIATIONS

This application is a continuation of Ser. No. 08/535,656 Sep. 28, 1995, Abandoned.

FIELD OF THE INVENTION

The present invention relates generally to obtaining physiological parameters from animals or humans, and more particularly to a system for deriving respiratory related information from a blood pressure signal obtained from either humans or animals.

BACKGROUND OF THE INVENTION

In animals or humans, it is often desirable to be able to monitor a variety of physiological parameters for purposes of research, therapeutics, and diagnosis. One such parameter that is of value is respiration. Simple measurement of the animal's or human's respiration rate have included the use of plethysmographs, strain gauges, chest impedance measurements, diaphragmatic EMG measurements, and other known measurement devices. For example in animal research, the plethysmograph approach requires the use of a non-compliant closed box in which the animal is placed with a means for measuring either the air flow in and out of the box or pressure changes inside the box or air flow at the animal's mouth when breathing air from outside or inside the closed container. While plethysmographs work reasonably well with human subjects who can cooperate with test personnel, it is unreliable when dealing with laboratory animals, such as rats, dogs, monkeys, and etc.

The use of strain gauges and apparatus for measuring chest impedance changes generally require the animal to be tethered to the test equipment via electrical leads and the like. This does not lend itself to chronic testing and, moreover, strain gauges are quite sensitive to movement artifacts that can mask the desired signal output. Diaphragmatic EMG measurements can be used to determine respiratory rate, but electrode placement requires a higher skilled surgeon, and electrical noise from ECG and other sources can make accurate detection of respiration difficult.

To allow for animal mobility, it has proven advantageous to surgically implant sensors within the animal along with a telemetry transmitter so that the sensed signals can be electronically transmitted to an external receiver without the need for exteriorized conductive leads or catheters. U.S. Pat. No. 4,846,191 to Brockway, et al., owned by applicant's assignee, describes an implantable blood pressure sensing and telemetering device suitable for long-term use in a variety of laboratory animals. A solid-state pressure sensor is fluid coupled to a selected blood vessel and the signal produced by the sensor is amplified, digitized and transmitted, transcutaneously, to an external receiver by means of a battery-powered transmitter. Once the blood pressure data are received, they are signal processed to recover features thereof, such as mean systolic pressure, mean diastolic pressure, mean arterial pressure, heart rate, etc. The Brockway et al. '191 patent also recognizes that the pressure sensing system used therein can be adapted to monitor intrathoracic pressure from which respiratory rate and other respiratory parameters can be derived. However, if it is desired to chronically monitor both blood pressure and respiratory activity following the teachings of the Brockway et al. patent, plural sensors and at least one telemetry transmitter with a multiplexing capability is required.

The Kahn et al. U.S. Pat. No. 4,860,759 demonstrates the combined use of transthoracic impedance and strain gauge sensors to monitor respiration rate. The approach disclosed in the Kahn et al. patent suffers from many shortcomings, not the least of which is the quality of the resulting data.

An example of the use of multiple, chronically implanted sensors in laboratory animals is described in R. Rubini et al., Power Spectrum Analysis of Cardiovascular Variability Monitored By Telemetry in Conscious, Unrestrained Rats, Journal of the Autonomic Nervous System, vol. 45, at 181–190 (1993). In the experiments described in the Rubini et al. paper, telemetry equipment manufactured by Data Sciences International (applicant's assignee) was utilized. However, the experimenters involved, while recognizing that a respiratory artifact was present in the sensed blood pressure data, discarded this component in favor of lower frequency components relating to sympathetic modulation of the cardiovascular system.

It is also known in the art that blood pressure is influenced by respiratory activity. In this regard, reference is made to H. Barthelmes and J. Eichmeier, A Device with Digital Display for the Determination of Respiratory Frequency from the Respiratory Fluctuations of Blood Pressure, Biomedizinische Technik, vol. 18, No. 4 (August 1973) and to D. Laude et. al., Effect of Breathing Pattern on Blood Pressure and Heart Rate Oscillations in Humans, Clinical and Experimental Pharmacology and Physiology, vol. 20, at 619–626 (1993). A system described in the Barthelmes paper employs an analog electronic filter to extract respiration rate from blood pressure signals. In the Laude article, human subjects were told to breath in rhythm with a metronome at several discrete frequencies while blood pressure was continuously measured. This study led to the conclusion that the relationship between systolic blood pressure and respiration differs from that between respiration and respiration sinus arrhythmia.

Although there are many studies in the published literature documenting variations of blood pressure with respiration, there is a need for an improved method and apparatus to derive respiratory parameters from blood pressure data.

SUMMARY OF THE INVENTION

The present invention provides a method and apparatus for obtaining physiologic parameter information of an animal or human other than blood pressure from a blood pressure signal indicative of sensed variations in blood pressure of the animal or human. The blood pressure signal is externally signal processed to develop an amplitude versus time waveform. A sequence of selected blood pressure features derived from individual cardiac cycles of the amplitude versus time waveform over a selected time interval are extracted from the developed amplitude versus time waveform. A mathematical model is fitted to the extracted sequence of selected blood pressure features to yield a fitted mathematical model. The physiologic parameter information is computed from the fitted mathematical model.

In a preferred embodiment of the present invention, the physiologic parameter information obtained is respiratory rate. In accordance with this preferred embodiment, a catheter tip of a blood pressure sensor is surgically implanted in an animal's vascular system where the sensor provides an electrical signal related to variations in the animal's blood pressure. A telemetry transmitter, also implanted in the animal, is connected to the blood pressure sensor for selectively transmitting a digitized version of the sensed electrical signal to an external receiver. The external receiver receives the digitized version of the sensed electrical signal and provides the blood pressure signal. The blood pressure signal is then signal processed in a digital computer to develop the amplitude versus time waveform, which is in a digitized form. The signal processing algorithm extracts from the digitized amplitude versus time waveform the sequence of selected blood pressure features such as beat-to-beat systolic data points, beat-to-beat diastolic data points, or beat-to-beat mean values of blood pressure over a predetermined time interval.

The mathematical model in this preferred embodiment is an $n^{th}$ order polynomial curve, which is preferably fitted to n+1 sequential points of the selected blood pressure features to obtain a fitted $n^{th}$ order polynomial curve. The fitted $n^{th}$ order polynomial curve preferably includes curve fit data values substantially equi-spaced in time. The curve fit data values are tested for critical points in accordance with a predetermined criteria such as a criteria relating peak values to zero-crossings of the fitted curve. Next, the computer determines from the critical points whether they are a maximum or a minimum whereby the respiratory rate can be determined from successive maximum and minimum critical points.

In one alternative embodiment of the present invention, spectral analysis is performed on the fitted mathematical model. In another alternative embodiment, several distinct blood pressure features for each cardiac cycle are combined to yield a sequence of averaged blood pressure features, and the mathematical model is then fitted to the resulting sequence of averaged blood pressure features.

The implantable pressure sensor/transmitter described in the Brockway et al. '191 patent referenced in the background section provides an excellent means for monitoring blood pressure. By appropriately signal processing the telemetered blood pressure waveforms, respiration rate and other physiologic parameters can be derived therefrom according to the present invention.

Accordingly, the present invention provides an improved system for monitoring a plurality of physiologic parameters in animals or humans using a single implanted telemetric sensor. Moreover, the present invention provides a system for measuring blood pressure and respiratory parameters in such animals or humans using a single telemetric sensor. The present invention also provides a system for extracting respiratory related physiologic data from animals or humans using an implanted blood pressure sensor and telemetry transmitter where the transmitted blood pressure signal is externally signal processed to recover the respiratory information contained in the blood pressure signal. It is not, however, necessary that the blood pressure data be telemetered. A blood pressure sensor could be connected via wires to an amplifier and analog-to-digital converter and then input into the computer-based system according to the present invention.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
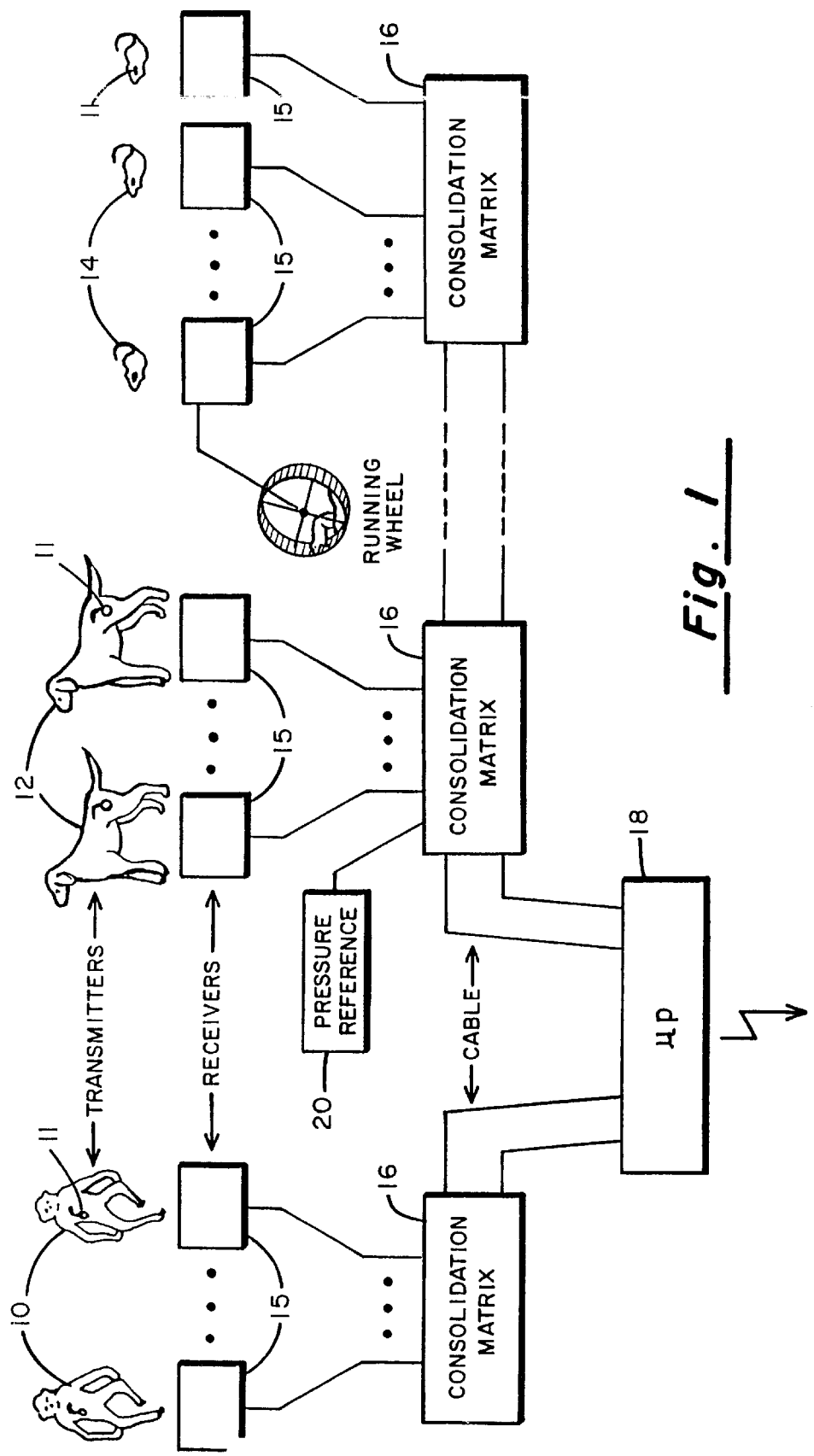
FIG. 1 is a system block diagram of a system according to the present invention for collecting and processing blood pressure related signals obtained from a plurality of lab animals to derive not only cardiovascular data, but also respiratory information.

Referring to the block diagram of FIG. 1, there is indicated a plurality of individual laboratory animals 10, 12 and 14 each having a blood pressure sensor and telemetry transmitter of the type described in the Brockway U.S. Pat. No. 4,846,191 implanted therein. These implanted modules are identified by numeral 11 in FIG. 1.

Disposed with or in proximity of each of the cages where the animals are kept is a telemetry receiver 15 which is tuned to pick up a signal transmitted from an individual animal. The individual receivers, in turn, are connected to multiplexers, as at 16, capable of servicing the number of individual receivers connected thereto, whereby data from a particular selected animal may be fed into the computer-based system 18 for collecting, storing, displaying, and analyzing data from a large plurality of animals.

In accordance with the present invention, the sensor/transmitters 11 are surgically implanted within the animals so as to monitor blood pressure in a predetermined blood vessel. The sensor/transmitter transmits bursts of pulses, the timing of which codes the magnitude of the analog blood pressure signal picked up by the sensor. Because the implanted units measure pressure relative to a vacuum, a pressure reference 20 is used to provide an input of the ambient barometric pressure to the computer-based system 18. By subtracting the ambient room pressure from the transmitter pressure readings, changes in barometric pressure can be accommodated.

Figure 2:
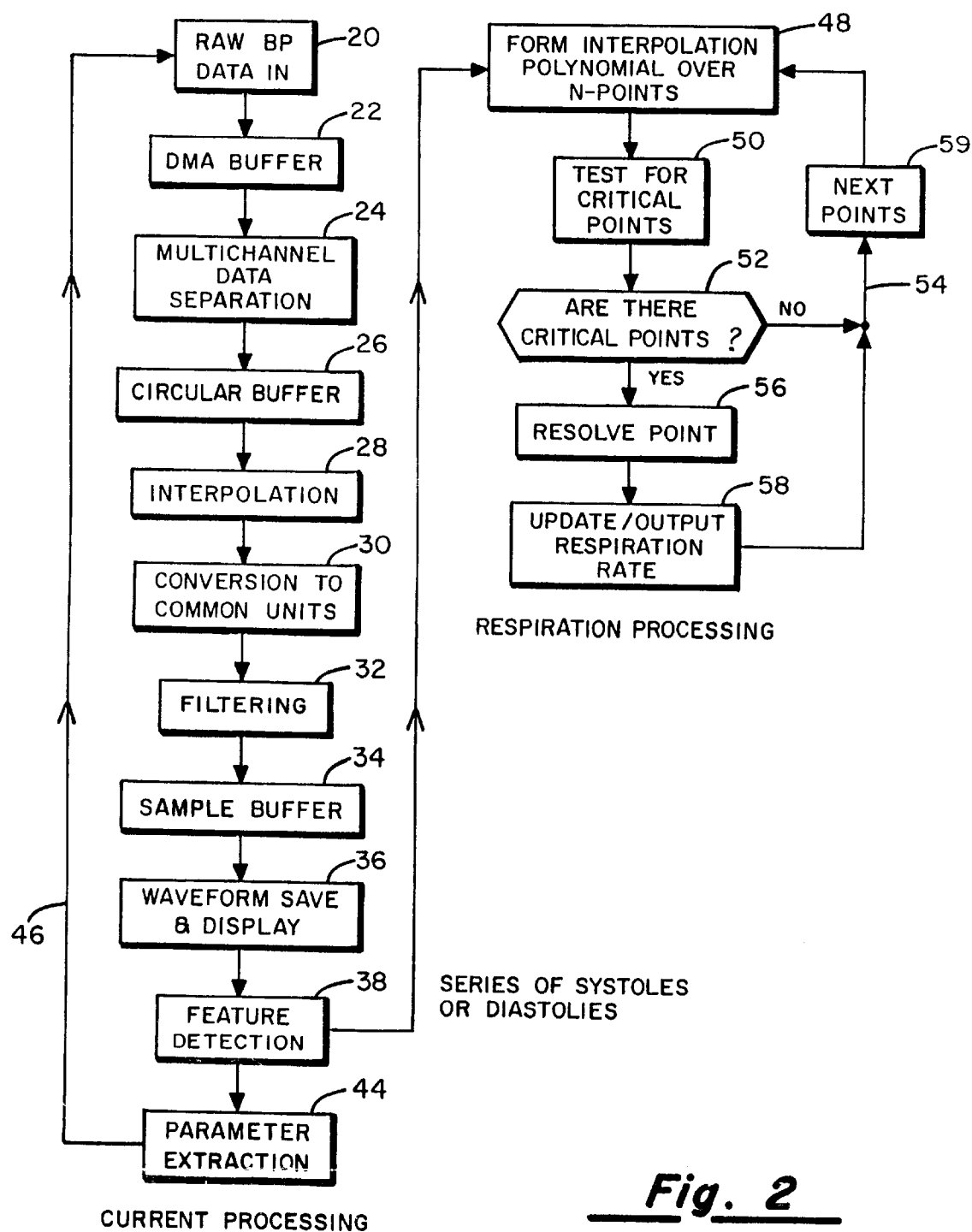
FIG. 2 is a software flow diagram illustrating the signal processing algorithm executed by the computer shown in FIG. 1 whereby the length of the respiratory cycle and therefore respiratory rate is obtained.

Turning now to FIG. 2, there is illustrated by means of a software flow diagram the algorithm executed by the computer-based system 18 for deriving both blood pressure information and respiratory information from the blood pressure measurements taken using the equipment illustrated in FIG. 1. This flow chart is in sufficient detail that persons skilled in programming an IBM PC or a clone thereof can write the source code for such a computer.

The first step in the algorithm identified by numeral 20 is to bring in the raw blood pressure data from an animal via the associated receiver 15 and consolidation matrix 16. This data is temporarily held in a DMA buffer (block 22) where it is maintained until called for by the program.

Had more than one sensor been implanted in the animal to provide measurements of more than one physiologic parameter, such as, for example, blood pressure and EKG, the data stream provided by the associated telemetry transmitter would include both channels of data. Hence, the software includes a routine for separating the multichannel data (block 24). In such an arrangement, a circular buffer is provided for each of the parameters being measured so that data from the individual channels can be separately stored (block 26). The data from a circular buffer, when selected, is processed in an interpolation algorithm (block 28), which converts the data to points substantially equi-spaced in time. The interval between successive points is set by the sample rate chosen in the software. It does so by fitting a third order polynomial of the form $y=ax^3+bx^2+cx+d$ to a series of four points comprising blood pressure readings at four different times. Continuing on with the assumption that it is the blood pressure parameter that has been sensed and is being processed, at block 30, the data are converted to appropriate units, e.g., mmHg. If noise is present in the interpolated data, it may be necessary to low pass filter the data to remove high frequency noise (block 32).

Figure 3:
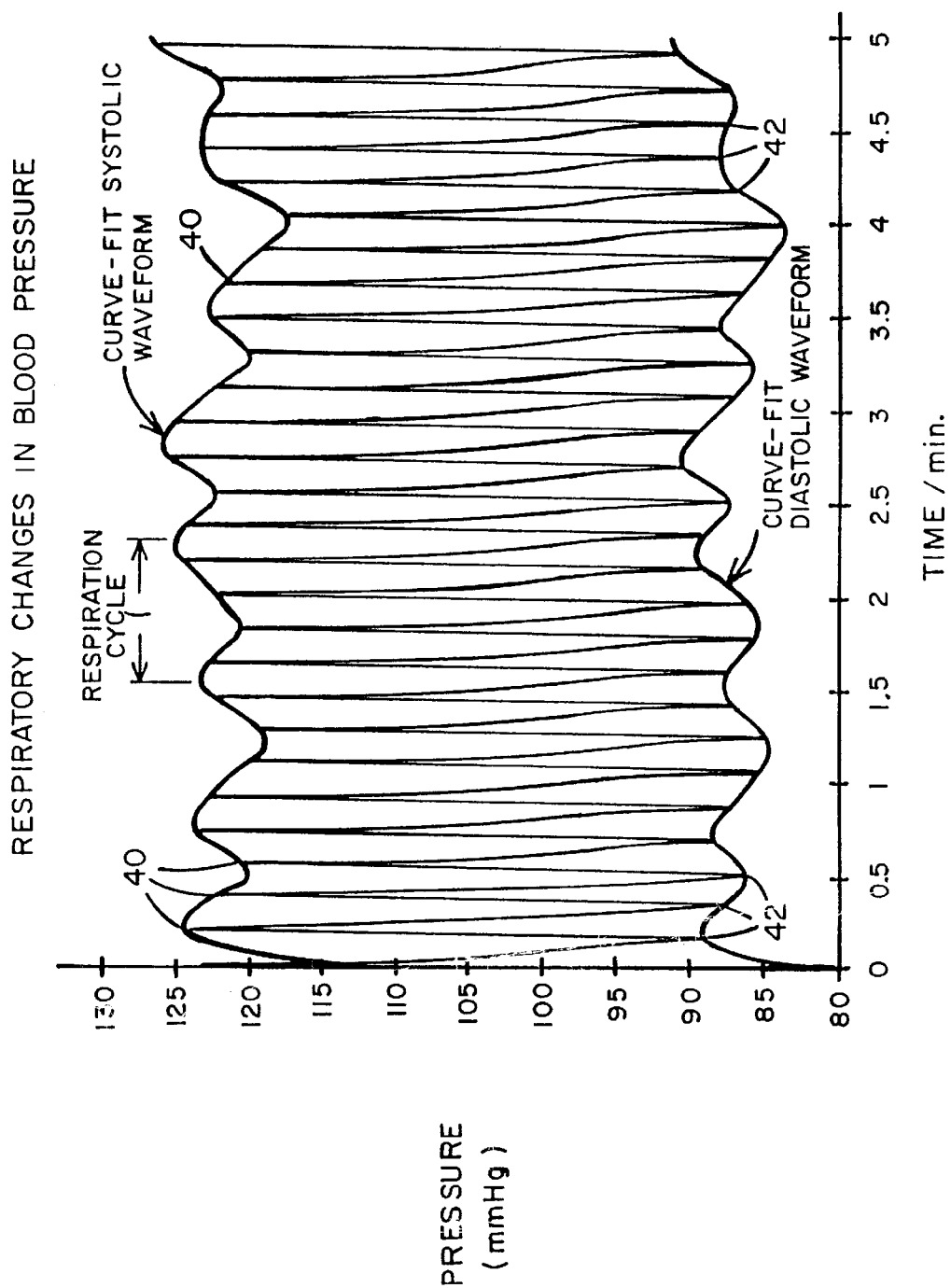
FIG. 3 is a graph illustrating a plot of blood pressure versus time showing a low frequency respiratory component of the blood pressure.

The resulting waveform data may again be held in a buffer (block 34) until called for. If desired, and as represented by block 36, the waveform can be saved on the computer's hard drive, a floppy-disk and/or presented on a computer display screen. The blood pressure waveform can be processed by a feature detection algorithm (block 38) in which the peaks, valleys, slopes, zero-crossings and the like are examined to extract information of value to the researcher, such as systole, diastole, heart rate and dP/dt. Referring to the waveform of FIG. 3, there is illustrated a plot of blood pressure measured in mmHg versus time for a five-second interval. The systolic points obtained as a result of the feature detection operation 38 are identified in FIG. 3 by numeral 40 and the diastolic valleys by numeral 42. The systolic points and diastolic points shown in FIG. 3 are illustrative of sequences of selected blood pressure features such as beat-to-beat systolic data points and beat-to-beat diastolic data points, but which can also include other blood pressure features such as beat-to-beat mean values of blood pressure over a predetermined time interval.

To obtain readings of the systolic and diastolic blood pressure, the points 40 and 42 may be averaged over a predetermined time interval such as, for example, 10 seconds which, in FIG. 2, is referred to as parameter extraction (block 44). Control loops back, via path 46, to the input of block 20 where further raw data telemetered from the implanted sensor or sensors is inputted for processing.

The algorithm represented by blocks 20 through 38 and 44 have been used in the past for deriving blood pressure parameters on an on-line and off-line basis. The present invention is concerned with the improvement whereby respiratory parameters may also be derived from the measured blood pressure signals obtained from the laboratory animals or alternatively from humans.

Referring again to FIG. 2, the series of systole points 40 obtained as a result of the feature detection operation 38 are supplied as inputs to another curve-fitting algorithm (block 48) which functions to add additional points between the peaks 40, thereby creating a smooth curve between adjacent systolic peaks in the blood pressure versus time waveform. The thus curve-fitted systolic waveform is labeled as such in FIG. 3. Once a third order curve has been fit to the data, the resulting waveform is tested for critical points based on a predetermined criteria (block 50). For example, the predetermined criteria in the preferred embodiment defines critical points at maximum excursions above a zero-crossing and/or peaks and valleys in the curve-fitted waveform. A test is made at decision block 52 whether a critical point has been reached and, if not, control exits via path 54 and further systole points are subjected to the curve-fitting algorithm at block 48.

When the test at decision block 52 indicates that a critical point has been reached, the operation performed at block 56 determines whether the critical point is a maximum or a minimum. By computing the interval between two adjacent maximums or two adjacent minimums, the length of a respiratory cycle is obtained. The inverse of this cycle length is respiratory rate, measured in breaths per second. The interval is continuously computed as represented by block 58 to provide a current, real-time indication of respiration rate. Although respiratory rate is a parameter of value and is the parameter derived in the preferred embodiment, the present invention is not limited to deriving respiratory rate from the curve-fit beat-beat data as the present invention can be applied to derive other physiologic parameters from the curve-fit beat-beat data.

It is seen that there is provided a method and apparatus to derive respiration rate and other physiologic parameters, either on-line or off-line from a continuous blood pressure signal. This is accomplished by way of a feature detection software algorithm. The capability of continuous waveform processing provides useful data relating to the respiratory system. In addition to on-line processing, the same pressure waveforms can be post-processed to derive respiration rate, other respiratory data, or other information related to other physiologic parameters which may be contained in the blood pressure waveform. The invention offers the advantage of obtaining data on more than one physiologic parameter, e.g., blood pressure and respiratory rate, using only a single sensor implanted in the animal.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. For example, the present invention is not limited to third order polynomials curves, as other $n^{th}$ order polynomials and other suitable mathematical models can be similarly fitted to blood pressure/time points according to the present invention. Likewise, it is not necessary that the blood pressure data be telemetered. A blood pressure sensor could, for example, transmit a signal indicative of blood pressure via LEDs or wires to an amplifier and analog-to-digital converter, which provides a blood pressure signal into the computer-based system according to the present invention.

When considering modifications to the preferred embodiment, it is to be understood that the respiratory-related information is obtainable by performing peak detection directly on the feature data without curve fitting, but since the data are not always ideal or equally spaced, it is difficult to resolve maximum and minimum points accurately as resolved by the present invention. Respiratory-related information is also obtainable by performing spectral analysis on the raw pressure waveform, but since the pressure data varies in frequency and amplitude, this approach is less than ideal in that it works best on truly periodic data. One could also signal process the data in accordance with the Barthelmes paper cited in the background section in which the raw blood pressure date is first high-pass filtered and then low-pass filtered. The Barthelmes approach, however, unlike the present invention, requires an optimal design of the filter and amplifier characteristics, be they digital or analog, to deal with a wide spectrum of data characteristics.

As to alternatives to the above described preferred embodiment, one embodiment of the present invention performs spectral analysis on the curve fit data values, such as the third order fitted curve, instead of performing the peak detection described above. Another embodiment of the present invention may achieve a more accurate indication of the respiratory effect on blood pressure by curve fitting the averaged systolic and diastolic values for each cardiac cycle before applying a peak detection to determine respiration rate. This approach is advantageous only when the systolic and diastolic curves remain completely in phase.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the mechanical, electromechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A method of obtaining respiratory parameter information of an animal or human from a blood pressure signal indicative of sensed variations in blood pressure of the animal or human, the method comprising the steps of:

signal processing, external from the animal or human, the blood pressure signal to develop an amplitude versus time waveform;

extracting from the developed amplitude versus time waveform a sequence of selected blood pressure features derived from individual cardiac cycles of the amplitude versus time waveform over a selected time interval;

fitting a mathematical model to the extracted sequence of selected blood pressure features to yield a fitted mathematical model of the blood pressure features; and computing the respiratory parameter information from the fitted mathematical model.

2. The method of claim 1 wherein the mathematical model is an $n^{th}$ order polynomial curve.

3. The method of claim 2 wherein n is at least equal to 3.

4. The method of claim 1 wherein the selected blood pressure features are selected from a group of blood pressure features including systolic data points, diastolic data points, and mean values of blood pressure for each cardiac cycle.

5. The method of claim 1 wherein the fitted mathematical model comprises curve fit data values substantially equal-spaced in time.

6. The method of claim 1 wherein the computing step includes the steps of:

testing the fitted mathematical model for critical points in accordance with a predetermined criteria;

determining from the critical points whether the critical points are a maximum or a minimum; and computing the respiratory parameter information from successive maximum and minimum critical points.

7. The method of claim 6 wherein the step of testing the fitted mathematical model for critical points includes locating peak values and zero-crossings of the fitted mathematical model.

8. The method of claim 1 wherein the respiratory parameter information is respiratory rate.

9. The method of claim 1 further comprising the steps of:

sensing variations in blood pressure from the animal or human and providing an electrical signal indicative of the sensed variations in blood pressure;

transmitting the electrical signal;

receiving, external to the animal or human, the transmitted signal and providing the blood pressure signal which is proportional to the transmitted signal.

10. The method of claim 9 further comprising the step of surgically implanting a blood pressure sensor and a transmitter in the animals's or human's vascular system, the sensor sensing the variations in blood pressure from the animal or human and providing the electrical signal indicative of the sensed variations in blood pressure to the transmitter which transmits the electrical signal.

11. The method of claim 1 wherein the signal processing step is performed by digitally signal processing the blood pressure signal.

12. The method of claim 1 wherein the computing step comprises the step of performing spectral analysis on the fitted mathematical model.

13. An apparatus for obtaining respiratory parameter information of an animal or human from a blood pressure signal indicative of sensed variations in blood pressure of the animal or human, the apparatus comprising:

an external signal processor for signal processing the blood pressure signal to develop an amplitude versus time waveform;

extracting means for extracting from the developed amplitude versus time waveform a sequence of selected blood pressure features derived from individual cardiac cycles of the amplitude versus time waveform over a selected time interval;

fitting means for fitting a mathematical model to the extracted sequence of selected blood pressure features to yield a fitted mathematical model of the blood pressure features; and computing means for computing the respiratory parameter information from the fitted mathematical model.

14. The apparatus of claim 13 wherein the mathematical model is an $n^{th}$ order polynomial curve.

15. The apparatus of claim 14 wherein n is at least equal to 3.

16. The apparatus of claim 13 wherein the selected blood pressure features are selected from a group of blood pressure features including systolic data points, diastolic data points, and means values of blood pressure for each cardiac cycle.

17. The apparatus of claim 13 wherein the fitted mathematical model comprises curve fit data values substantially equal-spaced in time.

18. The apparatus of claim 13 wherein the computing means includes:

means for testing the mathematical model for critical points in accordance with a predetermined criteria;

means for determining from the critical points whether the critical points are a maximum or a minimum; and means for computing the respiratory parameter information from successive maximum and minimum critical points.

19. The apparatus of claim 18 wherein the means for testing includes means for locating peak values and zero-crossings of the fitted mathematical model.

20. The apparatus of claim 13 wherein the respiratory parameter information is respiratory rate.

21. The apparatus of claim 13 further comprising:
a blood pressure sensor implantable in the animal or human to sense variations in blood pressure from the animal or human and provide an electrical signal indicative of the sensed variations in blood pressure;
a transmitter implantable in the animal or human to receive the electrical signal and to transmit the electrical signal from the animal or human; and
an external receiver for receiving the transmitted signal indicative of sensed variations in blood pressure of the animal or human and for providing the blood pressure signal proportional to the transmitted signal.

22. The apparatus of claim 13 wherein the external signal processor digitally signal processes the blood pressure signal.

23. The apparatus of claim 13 wherein the computing means includes means for performing spectral analysis on the fitted mathematical model.

* * * * *

UNITED STATES PATENT AND TRADEMARK OFFICE
CERTIFICATE OF CORRECTION

PATENT NO. : 6,299,582 B1
DATED : October 9, 2001
INVENTOR(S) : Brian P. Brockway, Robert V. Brockway and Richard A. Fundakowski It is certified that error appears in the above-identified patent and that said Letters Patent is hereby corrected as shown below:

Column 8,
Line 50, delete "means" and insert -- mean --, therefor.

Signed and Sealed this

Twenty-eighth Day of May, 2002

Attest:

Attesting Officer

JAMES E. ROGAN
Director of the United States Patent and Trademark Office